United States Patent
Alanine et al.

(10) Patent No.: US 7,368,454 B2
(45) Date of Patent: May 6, 2008

(54) (3,4-DIHYDRO-QUINAZOLIN-2-YL)-ARYL-AMINES

(75) Inventors: Alexander Alanine, Schlierbach (FR); Luca Claudio Gobbi, Oberwil (CH); Sabine Kolczewski, Rheinfelden (DE); Thomas Luebbers, Loerrach (DE); Jens-Uwe Peters, Grenzach-Wyhlen (DE); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/370,669

(22) Filed: Mar. 8, 2006

(65) Prior Publication Data

US 2006/0211716 A1 Sep. 21, 2006

(30) Foreign Application Priority Data

Mar. 15, 2005 (EP) .................... 05102001

(51) Int. Cl.
*A61K 31/517* (2006.01)
*C07D 239/84* (2006.01)

(52) U.S. Cl. .................. 514/266.4; 544/292
(58) Field of Classification Search ............. 514/266.4; 544/292
See application file for complete search history.

(56) References Cited

U.S. PATENT DOCUMENTS 3,496,179 A 2/1970 Hess et al. .......... 544/292
3,517,005 A 6/1970 Cronin et al. ....... 544/293

FOREIGN PATENT DOCUMENTS

WO WO 2004/096771 11/2004

OTHER PUBLICATIONS

Sprouse, J. "Pharmacological modulation of circadian rhythms . . . " Expert Opin. Ther. Targets (2004), vol. 8, No. 1, pp. 25-38.*
Hoyer, et al., Pharmacol. Rev. vol. 46, pp. 157-204 (1994).
Rees et al., FEBS Letters, vol. 355, pp. 242-246 (1994).
Francken et al., Eur. J. Pharmacol. vol. 361, pp. 299-309 (1998).
Noda, et al., J. Neurochem. vol. 84, pp. 222-232 (2003).
Dubertret et al., Journal of Psychiatric Research, vol. 38, pp. 371-376 (2004).
Garin, et al., Synthesis, pp. 375-376 (1983).
Garin, et al., Synthesis, p. 961 (1981).
Rahman, et al., Bioorganic & Medicinal Chemistry Letters, vol. 13, pp. 1119-1123 (2003).

* cited by examiner

*Primary Examiner*—James O. Wilson
*Assistant Examiner*—Tamthom N Truong
(74) *Attorney, Agent, or Firm*—George W. Johnston; Patricia S. Rocha-Tramaloni; Kimberly J. Prior

(57) ABSTRACT

The present invention relates to methods for treating $5\text{-HT}_{5A}$ receptor related diseases which comprises administering compounds of formula I

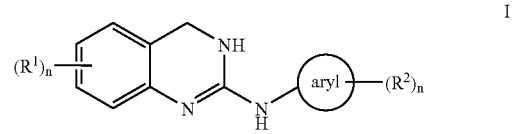

wherein
$R^1$, $R^2$, aryl, and n are defined in the specification and pharmaceutically acceptable acid addition salts thereof.

22 Claims, No Drawings

(3,4-DIHYDRO-QUINAZOLIN-2-YL)-ARYL-AMINES

PRIORITY TO RELATED APPLICATIONS

This application claims the benefit of European Application No. 05102001.4, filed Mar. 15, 2005, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides methods for treating 5-HT$_{5A}$ receptor related diseases by administering compounds of formula I

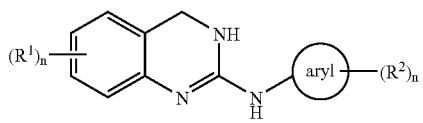

wherein
R$^1$ is hydrogen, lower alkyl or halogen;
R$^2$ is hydrogen, lower alkyl, lower alkoxy, halogen, lower alkyl substituted by halogen or cyano;
aryl is phenyl, naphthyl, or indan-5-yl; and
n is 1 or 2;

and pharmaceutically acceptable acid addition salts thereof.

The compounds disclosed by formula I are partially known. Related compounds have been described in U.S. Pat. Nos. 3,517,005 and 3,496,179, having bronchodilatory and/or hypotensive activities.

Compounds of formula I have good activity on the 5-HT$_{5A}$ receptor. Therefore, the invention provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771) which comprises administering a compound of formula I or a pharmaceutically acceptable salt thereof.

The preferred indications with regard to the present invention are the treatment of anxiety, depression, sleep disorders and schizophrenia.

DETAILED DESCRIPTION OF THE INVENTION

The following definitions of the general terms used in the present description apply irrespective of whether the terms in question appear alone or in combination. It should be understood that, as used in the specification and appended claims, the singular forms "a," "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl,2-butyl, t-butyl and the like. Preferred alkyl groups are groups with 1-4 carbon atoms.

The term "lower alkoxy" denotes a group wherein the alkyl residue is as defined above, and which is attached via an oxygen atom.

The term "halogen" denotes chlorine, iodine, fluorine and bromine.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective" denotes an amount that is effective to prevent, alleviate, or ameliorate symptoms of disease or prolong the survival of the subject being treated.

The present invention provides methods for treating 5-HT$_{5A}$ receptor related diseases by administering compounds of formula I

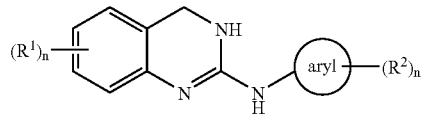

wherein
$R^1$ is hydrogen, lower alkyl or halogen;
$R^2$ is hydrogen, lower alkyl, lower alkoxy, halogen, lower alkyl substituted by halogen or cyano;
aryl is phenyl, naphthyl, or indan-5-yl; and
n is 1 or 2;

and pharmaceutically acceptable acid addition salts thereof.

Preferred compounds of formula I are those, wherein the aryl group is phenyl, for example the following compounds:
(5-methyl-3,4-dihydro-quinazolin-2-yl)-(3-trifluoromethyl-phenyl)-amine,
(3,4-dihydro-quinazolin-2-yl)-(3-trifluoromethyl-phenyl)-amine,
(5-chloro-3,4-dihydro-quinazolin-2-yl)-(3-trifluoromethyl-phenyl)-amine,
(3,4-dihydro-quinazolin-2-yl)-m-tolyl-amine,
(3-bromo-phenyl)-(3,4-dihydro-quinazolin-2-yl)-amine,
(5,6-dichloro-3,4-dihydro-quinazolin-2-yl)-(3-trifluoromethyl-phenyl)-amine,
(4-chloro-3-trifluoromethyl-phenyl)-(3,4-dihydro-quinazolin-2-yl)-amine,
(3-chloro-phenyl)-(3,4-dihydro-quinazolin-2-yl)-amine,
(3,5-bis-trifluoromethyl-phenyl)-(3,4-dihydro-quinazolin-2-yl)-amine,
(3,4-dihydro-quinazolin-2-yl)-(3-methoxy-phenyl)-amine and
(3,4-dihydro-quinazolin-2-yl)-(3-fluoro-phenyl)-amine.

Further preferred are compounds, wherein the aryl group is indan-5-yl, for example the following compound:
(3,4-dihydro-quinazolin-2-yl)-indan-5-yl-amine.

Preferred are further compounds, wherein the aryl group is naphthyl, for example (3,4-dihydro-quinazolin-2-yl)-naphthalen-1-yl-amine.

The present compounds of formula I and their pharmaceutically acceptable salts can be prepared by methods known in the art, for example by processes described below, which processes comprise a) reacting a compound of formula

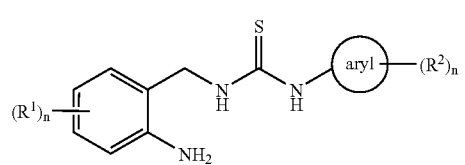

with MeI to obtain a compound of formula

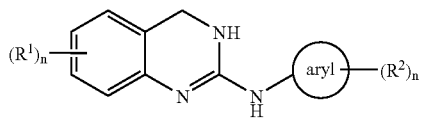

wherein $R^1$, $R^2$, aryl and n are as described above, or b) reacting a compound of formula

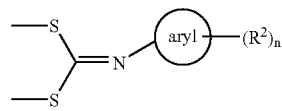

with a compound of formula

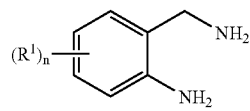

to obtain a compound of formula

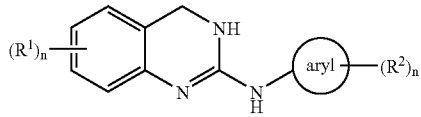

wherein $R^1$, $R^2$, aryl and n are as described above, and if desired, converting the compounds obtained into pharmaceutically acceptable acid addition salts.

In examples 1-23 and in the following schemes 1 and 2 the preparation of compounds of formula I is described in more detail. The starting materials are known compounds or can be prepared according to methods known in the art.

Scheme 1

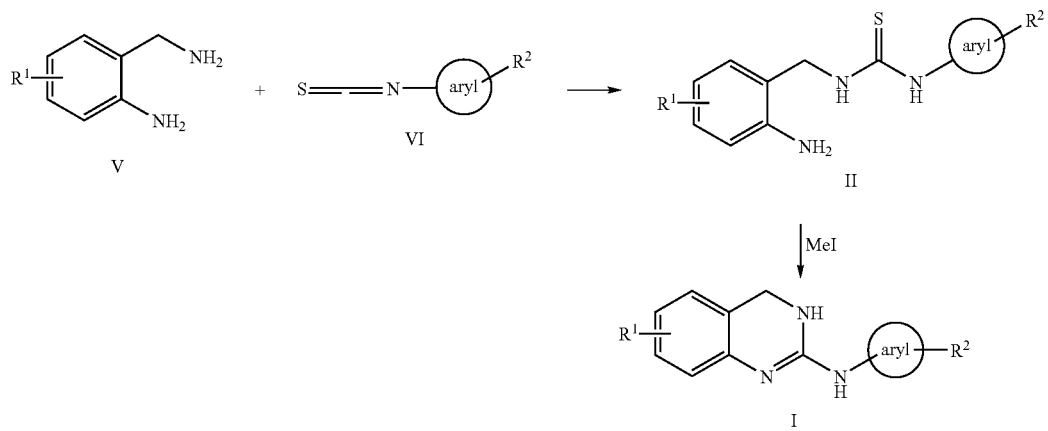

To a solution of a 2-aminobenzylamine of formula V in a solvent, such as ethyl acetate, an arylisothiocyanate of formula VI is added, and the mixture is heated for about 12 h. After cooling, the reaction mixture is concentrated, dried and purified in a conventional manner. To a solution of the obtained thiourea II in a solvent, such as ethanol, an alkylating agent, such as methyliodide, is added, and the mixture is heated to reflux for about 3 h. 3,4-Dihydro-quinazolin-2-yl)-aryl-amine I can be obtained from the reaction mixture by conventional purification.

Scheme 2

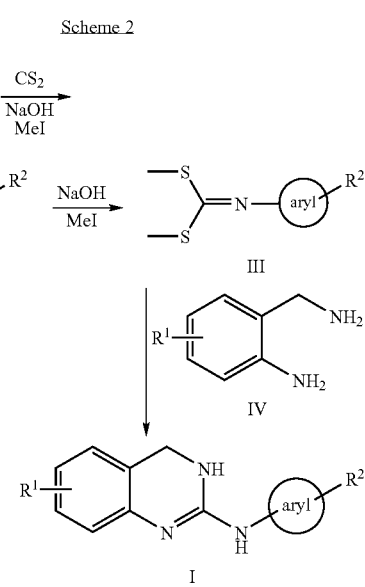

Aryldithiocarbamic acid methyl esters of formula VIII are prepared in close analogy to the method of J. Garin, V. Martinez, J. Mayoral, E. Melendez, F. Merchan: Synthesis 1981, 961. Aryldithiocarbonimidates of formula III are prepared in close analogy to the method of J. Garin, E. Melendez, F. L. Merchan, C. Tejel, and T. Tejero: Synthesis 1983, 375-376.

Carbon disulfide and a base, such as sodium hydroxide, are added to a solution of an arylamine VII in a suitable solvent, such as DMSO. After about 30min, methyl iodide is added, and the mixture is allowed to react for about 12 h. The reaction mixture is then worked up, and the obtained aryldithiocarbamic acid methyl ester VIII is purified in a conventional manner. A base, such as sodium hydroxide, and methyl iodide are then added to a solution of the obtained aryldithiocarbamic acid methyl ester VIII in a solvent, such as DMF, and the mixture is allowed to react for about 1.5 h. The reaction mixture is then worked up and purified in a conventional manner to give an aryldithiocarbonimidate of formula III. Compounds of formula III are heated with 2-benzylamines of formula IV and a suitable base, such as sodium hydroxide, in a solvent, such as DMSO, for about 3 h. (3,4-Dihydro-quinazolin-2-yl)-aryl-amines I are then isolated from the reaction mixture by conventional workup and purification.

As mentioned earlier, the compounds of formula I and their pharmaceutically usable addition salts possess valuable pharmaceutical properties. Compounds of the present invention are active on the 5-HT$_{5A}$ receptor and, therefore, are suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders and gastrointestinal disorders.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calculated using the Cheng-Prussoff equation.

The activity of the present compounds is described in the table below:

| Example | Ki (nM) |
|---------|---------|
| 1 | 85 |
| 2 | 91 |
| 3 | 118 |
| 4 | 143 |
| 5 | 149 |
| 6 | 155 |
| 10 | 300 |
| 15 | 990 |
| 16 | 1000 |

The present invention also provides pharmaceutical compositions containing compounds of the invention, for example compounds of formula I and their pharmaceutically acceptable salts, and a pharmaceutically acceptable carrier. Such pharmaceutical compositions can be in the form of tablets, coated tablets, dragées, hard and soft gelatine capsules, solutions, emulsions, or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers.

Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions, moreover, can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable salts thereof and, if desired, one or more other therapeutically valuable substances into a galenical administration form together with one or more therapeutically inert carriers.

As described above, compounds of the invention are active on the 5-HT$_{5A}$ receptor. The invention provides methods for treating depression (which includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders (which includes generalized anxiety and social anxiety disorder), schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome.

The most preferred indications in accordance with the present invention are those which include disorders of the central nervous system, for example the treatment of anxiety, depression, sleep disorders and schizophrenia. Thus, the invention provides a method of treating anxiety which comprises administering to an individual a therapeutically effective amount of a compound of formula I or a pharmaceutically acceptable salt thereof. The invention also provides a method of treating depression which comprises administering to an individual a therapeutically effective amount of a compound of formula I or a pharmaceutically acceptable salt thereof. The invention further provides a method of treating sleep disorders which comprises administering to an individual a therapeutically effective amount of a compound of formula I or a pharmaceutically acceptable salt thereof. The invention also provides a method of treating schizophrenia which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I may be prepared as shown in the following description:

EXAMPLE 1

(5-Methyl-3,4-dihydro-quinazolin-2-yl)-(3-trifluoromethyl-phenyl)-amine

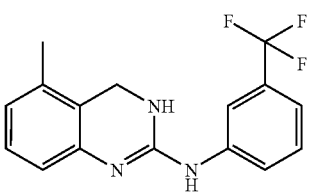

a) 1-(2-Amino-6-methyl-benzyl)-3-(3-trifluoromethyl-phenyl)-thiourea 3-(Trifluoromethyl)phenyl isothiocyanate (224 mg, 1.10 mmol) was added to a solution of 2-aminomethyl-3-methyl-phenylamine (150 mg, 1.10 mmol) in ethyl acetate (3 ml); the reaction mixture was shaken at 80° C. overnight in a screw-cap vial. For workup, more ethyl acetate was added, the mixture was washed with water and brine, and dried ($Na_2SO_4$). After evaporation of the solvent under reduced pressure, the title compound (50 mg, 13%) was obtained by purification of the residue (silica gel, heptan/ethyl acetate=100:0-80:20).

$^1$H NMR ($CDCl_3$): δ 2.30 (3H, s), 4.04 (2H, bs), 4.86 (2H, s), 6.22 (2H, bs), 6.56-6.61 (2H, m), 6.99-7.04 (1H, m), 7.37-7.42 (1H, m), 7.45-7.55 (3H, m).

b) (5-Methyl-3,4-dihydro-quinazolin-2-yl)-(3-trifluoromethyl-phenyl)-amine

A mixture of methyl iodide (167 mg, 1.18 mmol) and 1-(2-amino-6-methyl-benzyl)-3-(3-trifluoromethyl-phenyl)-thiourea (50 mg, 0.147 mmol) in ethanol (3 ml) was heated to reflux for 3 h. The solvent was evaporated under reduced pressure, the residue was taken up in ethyl acetate, washed (water), and dried ($Na_2SO_4$). After evaporation of the solvent under reduced pressure, the title compound (4 mg, 8.9%, MS: m/e=306.1 [M+H$^+$]) was obtained by HPLC purification of the residue (YMC CombiPrep C18 column 50×20 mm, solvent gradient 5-95% $CH_3CN$ in 0.1% TFA (aq) over 6.0 min, λ=230 nm, flow rate 40 ml/min).

EXAMPLE 2

(3,4-Dihydro-quinazolin-2-yl)-(3-trifluoromethyl-phenyl)-amine

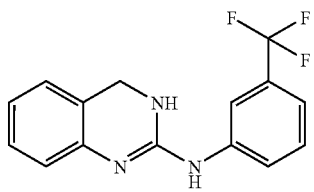

a) (3-Trifluoromethyl-phenyl)-dithiocarbamic acid methyl ester

Under an atmosphere of nitrogen, carbon disulfide (0.73 ml, 12 mmol) was added to a solution of 3-aminobenzotrifluoride (1.50 g, 9.3 mmol) in DMSO (10 ml). Subsequently, sodium hydroxide (0.56 ml, solution in water, 20 mol/l, 11 mmol) was added, and the dark brown reaction mixture was stirred for 30 min (r.t.). Upon the addition of methyl iodide (730 ml, 12 mmol), the mixture turned yellow and was stirred overnight (r.t.). The reaction mixture was poured into water and extracted with ethyl acetate. The extract was dried ($Na_2SO_4$), and the solvent evaporated under reduced pressure. The title compound (1.65 g, 71%) was obtained by purification of the residue (silica gel, heptan/ethyl acetate=100:0-80:20).

$^1$H NMR ($CDCl_3$): δ 2.69 (3H, s), 7.55 (2H, m), 7.74 (1H, m), 7.8 (1H, m), 8.76 (1H, bs).

b) (3-Trifluoromethyl-phenyl)-dimethyl-dithiocarbonimidate

Under an atmosphere of nitrogen, sodium hydroxide (0.39 ml, solution in water, 20 mol/l, 8 mmol) was added to a solution of (3-trifluoromethyl-phenyl)-dithiocarbamic acid methyl ester (1.65 g, 6.57 mmol) in DMF (10 ml). Methyl iodide (0.53 ml, 8.52 mmol) was then added, and the mixture was stirred for 1.5 h (r.t.). The mixture was taken up in ethyl acetate, washed (water), and dried ($Na_2SO_4$). Upon the evaporation of the solvent under reduced pressure, the title compound (1.50 g, 86%) was isolated by purification of the residue (silica gel, heptan/ethyl acetate=100:0-90:10).

$^1$H NMR ($CDCl_3$): δ 2.52 (6H, s), 7.04 (1H, d, J=8Hz), 7.14 (1H, s), 7.35 (1H, d, J=7Hz), 7.40 (1H, dd, J=8Hz, 7Hz).

c) (3,4-Dihydro-quinazolin-2-yl)-(3-trifluoromethyl-phenyl)-amine

Under an atmosphere of nitrogen, sodium hydroxide (0.1 ml, solution in water, 20 mol/l, 2 mmol) was added to a solution of 2-aminobenzylamine (92 mg, 0.75 mmol) in DMSO (1 ml). After 30 min, a solution of (3-trifluoromethyl-phenyl)-dimethyl-dithiocarbonimidate (200 mg, 0.75 mmol) in DMSO (1 ml) was added, and the mixture was heated to 190° C. for 3 h. The title compound (50 mg, 23%, MS: m/e=292.1 [M+H$^+$]) was isolated from the reaction mixture by preparative, reverse phase HPLC (YMC CombiPrep C18 column 50×20 mm, solvent gradient 5-95% $CH_3CN$ in 0.1% TFA(aq) over 6.0 min, λ=230 nm, flow rate 40 ml/min).

EXAMPLE 3

(5-Chloro-3,4-dihydro-quinazolin-2-yl)-(3-trifluoromethyl-phenyl)-amine

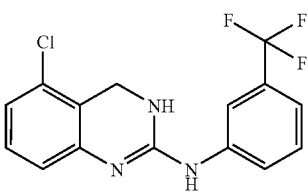

The title compound (MS: m/e=326.3 [M+H$^+$]) was prepared in analogy to example 1 from 2-amino-6-chlorobenzylamine.

EXAMPLE 4

(3,4-Dihydro-quinazolin-2-yl)-m-tolyl-amine

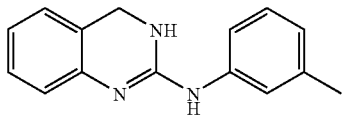

The title compound (MS: m/e=238.3 [M+H$^+$]) was prepared in analogy to example 2 from 2-aminobenzylamine and m-toluidine.

EXAMPLE 5

(3,4-Dihydro-quinazolin-2-yl)-indan-5-yl-amine

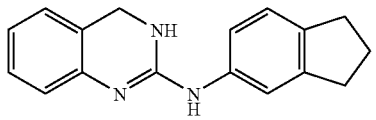

The title compound (MS: m/e=264.4 [M+H$^+$]) was prepared in analogy to example 2 from 2-aminobenzylamine and 5-aminoindane.

EXAMPLE 6

(3,4-Dihydro-quinazolin-2-yl)-naphthalen-1-yl-amine

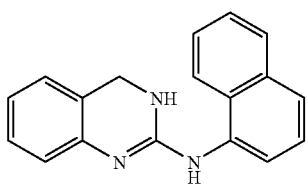

The title compound (MS: m/e=274.2 [M+H$^+$]) was prepared in analogy to example 2 from 2-aminobenzylamine and 1-naphtylamine.

EXAMPLE 7

(3-Bromo-phenyl)-(3,4-dihydro-quinazolin-2-yl)-amine

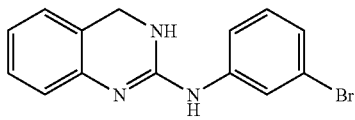

The title compound (MS: m/e=302.1 [M+H$^+$]) was prepared in analogy to example 2 from 2-aminobenzylamine and 3-bromoaniline.

EXAMPLE 8

(5,6-Dichloro-3,4-dihydro-quinazolin-2-yl)-(3-trifluoromethyl-phenyl)-amine

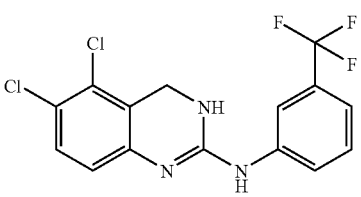

The title compound (MS: m/e=360.0 [M+H$^+$]) was prepared in analogy to example 1 from 2-amino-5,6-dichlorobenzylamine.

EXAMPLE 9

(4-Chloro-3-trifluoromethyl-phenyl)-(3,4-dihydro-quinazolin-2-yl)-amine; hydriodide

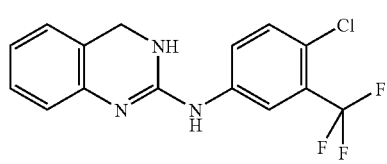

The title compound (MS: m/e=326.3 [M+H$^+$]) was prepared in analogy to example 1 from 2-aminobenzylamine and 4-chloro-3-(trifluoromethyl)phenyl isothiocyanate. Instead of HPLC purification in step c), the final product was isolated from the reaction mixture by filtration.

EXAMPLE 10

(3-Chloro-phenyl)-(3,4-dihydro-quinazolin-2-yl)-amine

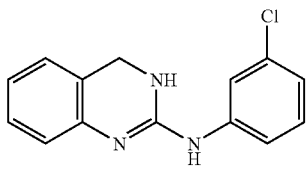

The title compound (MS: m/e=258.0 [M+H$^+$]) was prepared in analogy to example 2 from 2-aminobenzylamine and 3-chloroaniline.

EXAMPLE 11

(3,5-Bis-trifluoromethyl-phenyl)-(3,4-dihydro-quinazolin-2-yl)-amine

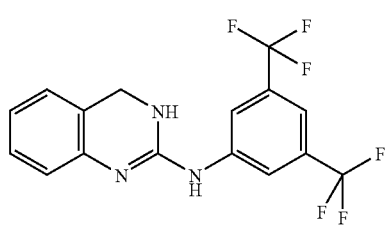

The title compound (MS: m/e=360.2 [M+H$^+$]) was prepared in analogy to example 1 from 2-aminobenzylamine and 3,5-trifluorophenylisothiocyanate.

EXAMPLE 12

(3,4-Dihydro-quinazolin-2-yl)-(3-methoxy-phenyl)-amine

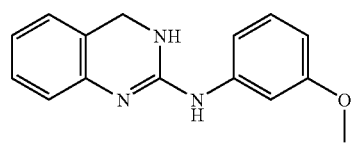

The title compound (MS: m/e=254.1 [M+H$^+$]) was prepared in analogy to example 1 from 2-aminobenzylamine and 3-methoxyphenylisothiocyanate.

EXAMPLE 13

(3,4-Dihydro-quinazolin-2-yl)-(3-fluoro-phenyl)-amine; hydriodide

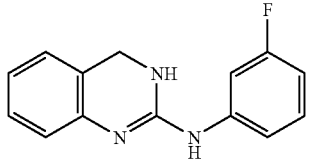

The title compound (MS: m/e=242.0 [M+H$^+$]) was prepared in analogy to example 1 from 2-aminobenzylamine and 3-fluorophenylisothiocyanate. Instead of HPLC purification in step c), the final product was isolated from the reaction mixture by filtration.

EXAMPLE 14

(3,4-Dihydro-quinazolin-2-yl)-(4-fluoro-phenyl)-amine; hydriodide

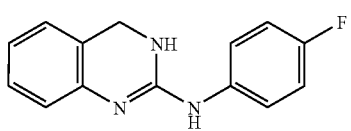

The title compound (MS: m/e=242.2 [M+H$^+$]) was prepared in analogy to example 1 from 2-aminobenzylamine and 4-fluorophenylisothiocyanate. Instead of HPLC purification in step c), the final product was isolated from the reaction mixture by filtration.

EXAMPLE 15

(4-Chloro-phenyl)-(3,4-dihydro-quinazolin-2-yl)-amine

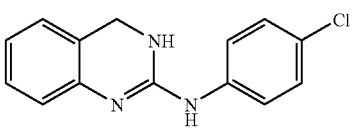

The title compound (MS: m/e=257.9 [M+H$^+$]) was prepared in analogy to example 1 from 2-aminobenzylamine and 4-chlorophenylisothiocyanate.

EXAMPLE 16

(3,4-Dihydro-quinazolin-2-yl)-(2-fluoro-phenyl)-amine; hydriodide

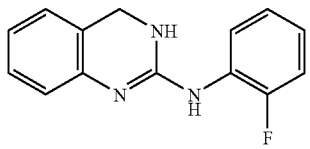

The title compound (MS: m/e=242.3 [M+H⁺]) was prepared in analogy to example 1 from 2-aminobenzylamine and 2-fluorophenylisothiocyanate. Instead of HPLC purification in step c), the final product was isolated from the reaction mixture by filtration.

EXAMPLE 17

3-(3,4-Dihydro-quinazolin-2-ylamino)-benzonitrile; hydriodide

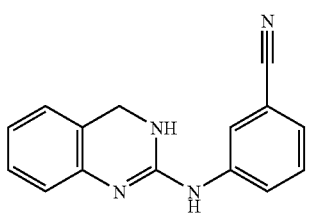

The title compound (MS: m/e=249.1 [M+H⁺]) was prepared in analogy to example 1 from 2-aminobenzylamine and 3-cyanophenylisothiocyanate. Instead of HPLC purification in step c), the final product was isolated from the reaction mixture by filtration.

EXAMPLE 18

(3,4-Dihydro-quinazolin-2-yl)-o-tolyl-amine

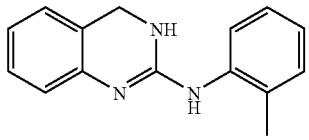

The title compound (MS: m/e=238.3 [M+H⁺]) was prepared in analogy to example 1 from 2-aminobenzylamine and 2-methylphenylisothiocyanate.

EXAMPLE 19

(2-Chloro-phenyl)-(3,4-dihydro-quinazolin-2-yl)-amine

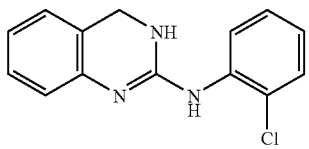

The title compound (MS: m/e=258.0 [M+H⁺]) was prepared in analogy to example 2 from 2-aminobenzylamine and 2-chloroaniline.

EXAMPLE 20

(3,4-Dihydro-quinazolin-2-yl)-p-tolyl-amine

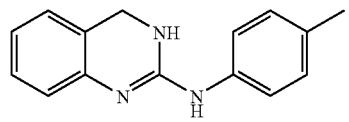

The title compound (MS: m/e=238.3 [M+H⁺]) was prepared in analogy to example 1 from 2-aminobenzylamine and 4-methylphenylisothiocyanate.

EXAMPLE 21

4-(3,4-Dihydro-quinazolin-2-ylamino)-benzonitrile

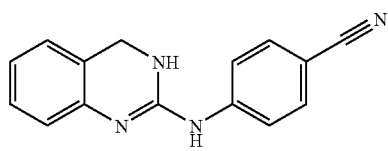

The title compound (MS: m/e=249.0 [M+H⁺]) was prepared in analogy to example 1 from 2-aminobenzylamine and 4-cyanophenylisothiocyanate.

EXAMPLE 22

(3,4-Dihydro-quinazolin-2-yl)-(2-methoxy-phenyl)-amine

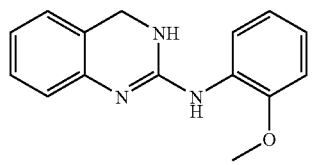

The title compound (MS: m/e=254.2 [M+H⁺]) was prepared in analogy to example 2 from 2-aminobenzylamine and o-anisidine.

EXAMPLE 23

(3,4-Dihydro-quinazolin-2-yl)-(4-methoxy-phenyl)-amine; hydriodide

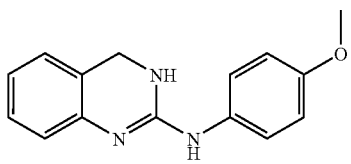

The title compound (MS: m/e=254.1 [M+H⁺]) was prepared in analogy to example 2 from 2-aminobenzylamine and p-anisidine. Instead of HPLC purification in step c), the final product was isolated from the reaction mixture by filtration.

The invention claimed is:

1. A method of treating schizophrenia comprising administering to an individual a therapeutically effective amount of a compound of formula I

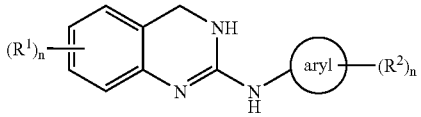

wherein
  $R^1$ is hydrogen, lower alkyl, or halogen;
  $R^2$ is hydrogen, lower alkyl, lower alkoxy, halogen, lower alkyl substituted by halogen, or cyano;
  aryl is phenyl, naphthyl or indan-5-yl; and
  n is 1 or 2;
or a pharmaceutically acceptable acid addition salt thereof.

2. The method of claim 1, wherein the aryl is phenyl.

3. The method of claim 2, wherein the compound is selected from the group consisting of
  (5-methyl-3,4-dihydro-quinazolin-2-yl)-(3-trifluoromethyl-phenyl)-amine,
  (3,4-dihydro-quinazolin-2-yl)-(3-trifluoromethyl-phenyl)-amine,
  (5-chloro-3,4-dihydro-quinazolin-2-yl)-(3-trifluoromethyl-phenyl)-amine,
  (3,4-dihydro-quinazolin-2-yl)-m-tolyl-amine,
  (3-bromo-phenyl)-(3,4-dihydro-quinazolin-2-yl)-amine,
  (5,6-dichloro-3,4-dihydro-quinazolin-2-yl)-(3-trifluoromethyl-phenyl)-amine,
  (4-chloro-3-trifluoromethyl-phenyl)-(3,4-dihydro-quinazolin-2-yl)-amine,
  (3-chloro-phenyl)-(3,4-dihydro-quinazolin-2-yl)-amine,
  (3,5-bis-trifluoromethyl-phenyl)-(3,4-dihydro-quinazolin-2-yl)-amine,
  (3,4-dihydro-quinazolin-2-yl)-(3-methoxy-phenyl)-amine and
  (3,4-dihydro-quinazolin-2-yl)-(3-fluoro-phenyl)-amine.

4. The method of claim 1, wherein aryl is indan-5-yl.

5. The method of claim 4, wherein the compound is (3,4-dihydro-quinazolin-2-yl)-indan-5-yl-amine.

6. The method of claim 1, wherein aryl is naphthyl.

7. The method of claim 6, wherein the compound is (3,4-dihydro-quinazolin-2-yl)-naphthalen-1-yl-amine.

8. A process for preparing a compound of formula I

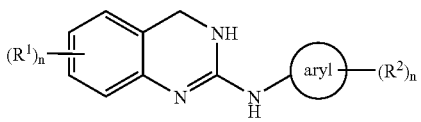

wherein
  $R^1$ is hydrogen, lower alkyl, or halogen;
  $R^2$ is hydrogen, lower alkyl, lower alkoxy, halogen, lower alkyl substituted by halogen, or cyano;
which process is selected from the group consisting of
  a) reacting a compound of formula II

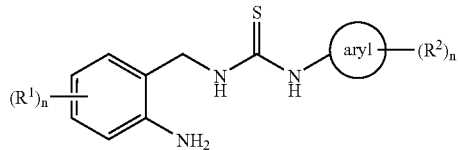

with MeI
to obtain a compound of formula

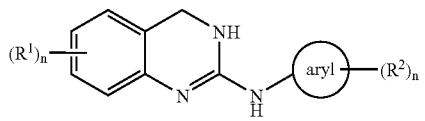

and b) reacting a compound of formula

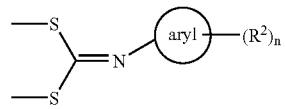

with a compound of formula

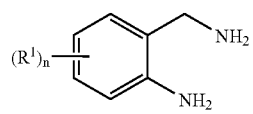

to obtain a compound of formula

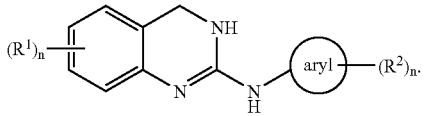

9. A method of treating sleep disorders related to circadian rhythm comprising administering to an individual a therapeutically effective amount of a compound of formula I

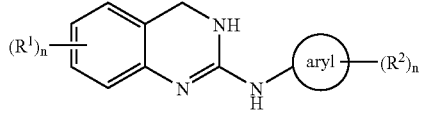

wherein
  $R^1$ is hydrogen, lower alkyl, or halogen;
  $R^2$ is hydrogen, lower alkyl, lower alkoxy, halogen, lower alkyl substituted by halogen, or cyano;
  aryl is phenyl, naphthyl or indan-5-yl; and
  n is 1 or 2;
or a pharmaceutically acceptable acid addition salt thereof.

10. The method of claim 9, wherein the aryl is phenyl.

11. The method of claim 10, wherein the compound is selected from the group consisting of
(5-methyl-3,4-dihydro-quinazolin-2-yl)-(3-trifluoromethyl-phenyl)-amine,
(3,4-dihydro-quinazolin-2-yl)-(3-trifluoromethyl-phenyl)-amine,
(5-chloro-3,4-dihydro-quinazolin-2-yl)-(3-trifluoromethyl-phenyl)-amine,
(3,4-dihydro-quinazolin-2-yl)-m-tolyl-amine,
(3-bromo-phenyl)-(3,4-dihydro-quinazolin-2-yl)-amine,
(5,6-dichloro-3,4-dihydro-quinazolin-2-yl)-(3-trifluoromethyl-phenyl)-amine,
(4-chloro-3-trifluoromethyl-phenyl)-(3,4-dihydro-quinazolin-2-yl)-amine,
(3-chloro-phenyl)-(3,4-dihydro-quinazolin-2-yl)-amine,
(3,5-bis-trifluoromethyl-phenyl)-(3,4-dihydro-quinazolin-2-yl)-amine,
(3,4-dihydro-quinazolin-2-yl)-(3-methoxy-phenyl)-amine and
(3,4-dihydro-quinazolin-2-yl)-(3-fluoro-phenyl)-amine.

12. The method of claim 9, wherein aryl is indan-5-yl.

13. The method of claim 12, wherein the compound is (3,4-dihydro-quinazolin-2-yl)-indan-5-yl-amine.

14. The method of claim 9, wherein aryl is naphthyl.

15. The method of claim 14, wherein the compound is (3,4-dihydro-quinazolin-2-yl)-naphthalen-1-yl-amine.

16. A method of treating a disorder selected from the group consisting of anxiety and depression comprising administering to an individual a therapeutically effective amount of a compound of formula I

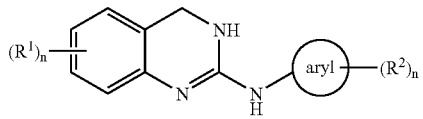

wherein
$R^1$ is hydrogen, lower alkyl, or halogen;
$R^2$ is hydrogen, lower alkyl, lower alkoxy, halogen, lower alkyl substituted by halogen, or cyano;
aryl is phenyl, naphthyl or indan-5-yl; and
n is 1 or 2;
or a pharmaceutically acceptable acid addition salt thereof.

17. The method of claim 16, wherein the aryl is phenyl.

18. The method of claim 17, wherein the compound is selected from the group consisting of
(5-methyl-3,4-dihydro-quinazolin-2-yl)-(3-trifluoromethyl-phenyl)-amine,
(3,4-dihydro-quinazolin-2-yl)-(3-trifluoromethyl-phenyl)-amine,
(5-chloro-3,4-dihydro-quinazolin-2-yl)-(3-trifluoromethyl-phenyl)-amine,
(3,4-dihydro-quinazolin-2-yl)-m-tolyl-amine,
(3-bromo-phenyl)-(3,4-dihydro-quinazolin-2-yl)-amine,
(5,6-dichloro-3,4-dihydro-quinazolin-2-yl)-(3-trifluoromethyl-phenyl)-amine,
(4-chloro-3-trifluoromethyl-phenyl)-(3,4-dihydro-quinazolin-2-yl)-amine,
(3-chloro-phenyl)-(3,4-dihydro-quinazolin-2-yl)-amine,
(3,5-bis-trifluoromethyl-phenyl)-(3,4-dihydro-quinazolin-2-yl)-amine,
(3,4-dihydro-quinazolin-2-yl)-(3-methoxy-phenyl)-amine and
(3,4-dihydro-quinazolin-2-yl)-(3-fluoro-phenyl)-amine.

19. The method of claim 16, wherein aryl is indan-5-yl.

20. The method of claim 19, wherein the compound is (3,4-dihydro-quinazolin-2-yl)-indan-5-yl-amine.

21. The method of claim 16, wherein aryl is naphthyl.

22. The method of claim 21, wherein the compound is (3,4-dihydro-quinazolin-2-yl)-naphthalen-1-yl-amine.

* * * * *